US006626817B2

United States Patent
Lüth

(12) United States Patent
(10) Patent No.: US 6,626,817 B2
(45) Date of Patent: Sep. 30, 2003

(54) METHOD AND APPARATUS FOR POSITIONING AND DISCHARGING RADIATION SOURCES IN BIOLOGICAL TISSUE BY WAY OF HOLLOW NEEDLES

(75) Inventor: Tim Lüth, Berlin (DE)

(73) Assignee: Jojumarie Intelligente Instrumente GmbH, Berlin (DE)

(*) Notice: Subject to any disclaimer, the term of this patent is extended or adjusted under 35 U.S.C. 154(b) by 0 days.

(21) Appl. No.: 09/990,071

(22) Filed: Nov. 21, 2001

(65) Prior Publication Data

US 2002/0120175 A1 Aug. 29, 2002

(51) Int. Cl.[7] ............................. A61N 5/00; A61N 1/30
(52) U.S. Cl. .......................................... 600/7; 604/19
(58) Field of Search ......................... 600/1–8; 376/158, 376/169, 184, 186, 202; 604/19

(56) References Cited

U.S. PATENT DOCUMENTS

| | | | |
|---|---|---|---|
| 5,342,283 A | * | 8/1994 | Good ............................ 600/8 |
| 5,460,592 A | | 10/1995 | Langton et al. |
| 5,860,909 A | | 1/1999 | Mick et al. |
| 5,906,574 A | | 5/1999 | Kan |
| 5,938,583 A | | 8/1999 | Grimm |
| 6,010,446 A | | 1/2000 | Grimm |
| 6,102,844 A | | 8/2000 | Ravins et al. |

FOREIGN PATENT DOCUMENTS

WO    WO 00/61229    10/1900

* cited by examiner

Primary Examiner—Eric F. Winakur
Assistant Examiner—Nikita R Veniaminov
(74) Attorney, Agent, or Firm—Kenyon & Kenyon

(57) ABSTRACT

A method for the positioning of radiation source seeds, spacer seeds and stoppers in tissue using hollow needles. Various seeds that are separately contained in magazines according to the isotope type (e.g., material, dosage, half-life period), are provided to the hollow needle. The individual magazines may be changed by means of a magazine changer. The magazine changer is located in a changer guide in a position which is vertical relative to the direction of injection of the seeds. The location of the needle is measured relative to a location reference block. An optimal seed deposit position is detected acoustically and/or visually and/or in a tactile manner. The selection of a magazine and a seed to be discharged from the magazine is derived from the current position of the needle in the tissue and from a treatment plan for a dosage distribution, which may be established in list form with details on the seed type and the x-y-z-coordinates relative to the location reference block.

20 Claims, 3 Drawing Sheets

METHOD AND APPARATUS FOR POSITIONING AND DISCHARGING RADIATION SOURCES IN BIOLOGICAL TISSUE BY WAY OF HOLLOW NEEDLES

RELATED APPLICATIONS

The present application claims the benefit of priority to Applicant's co-pending German Patent Application No. 10058163.3, filed in Germany on Nov. 22, 2000.

1. Field of the Invention

The present invention relates to a method and an apparatus for positioning radiation sources by way of hollow needles for the purpose of achieving an optimal dosage distribution during the introduction of various radiation sources in biological tissue. The method and the apparatus are particularly well suited for the treatment of prostate cancer with weak radioactive radiation sources (e.g., seeds).

2. Background of the Invention

In brachytherapy, tumour tissue is subjected to radiation from the shortest possible distance. This is accomplished, for example, with small radioactive and/or gamma-radiating sources which are inserted by way of hollow needles into the tumour tissue. Conventionally, a tumour is punctured by several hollow needles. In this particular case, two different methods of treating tumour tissue are typically employed.

According to a first method, a radiation source having a strong dosage of radiation is exposed to the tumour tissue. The radiation sources are put into the needles for a short period and are then taken out again. The radiation is discharged through the wall of the hollow needles. The treatment is repeated as required. The radiation sources have a very large half-life period in the magnitude of years.

According to a second method, a radiation source having a low dosage of radiation is exposed to the tumour tissue. The seeds are grain size and are discharged or implanted through the hollow needles into the tissue. The seeds remain in the tissue. The half-life period of these radiation sources amount to weeks and/or months and, during this period, the radiation drops below a therapeutic or harmful effect. For the treatment of the tumour tissue, for example, weak radioactive isotopes of the elements iodine, cobalt or palladium are typically applied.

In this second case, it is important, in order to achieve the greatest therapeutic benefit, that the dosage distribution be as uniform as possible and be located in the tumour tissue (e.g., prostate tissue) at a high level.

It is also important that the healthy tissue (e.g., the urethra tissue, the seminal vesicle tissue, etc.) shall not be subjected to radiation above a maximum dosage, which may cause renewed or protracted diseases of the healthy tissues.

In conventional systems, an amount of similar seeds having the same radiation dosage and half-life period are typically placed in the tumour tissue. In order tomaximize the therapeutic benefits, a software for dosage planning may be employed. The software determines the positions of the seeds in a Cartesian coordinate system relative to an extracorporally secured perforated raster plate. In a conventional system, the perforated raster has a 5 mm clearance between the holes. The needles for the seed implantation are guided through the perforated raster in accordance with the specified details of the dosage planning software. They are inserted through the skin and healthy tissue and into the tumour tissue. For depth checking purposes, either a scale applied to the needles is adopted or a mechanical scale in addition to the needle is employed.

Conventionally, there are two basic methods for inserting the seeds. According to a first method, the insertion is performed by inserting hollow needles which are loaded up to the needle tip with a seed strand (e.g., RAPID STRAND™) made up of similarly therapeutic seeds. The seed strand is then anchored at the needle tip in the tissue and the needle is withdrawn. In this case, the seed strand remains in the tissue.

Two methods for the manufacture and the use of seed strands are typically employed. U.S. Pat. No. 5,460,592 to Langton et al. discloses a device for the manufacture and transport of seeds that are embedded in a bio-absorbable material. After an intervention planning, the strands are taken from a transport vessel and shortened to the required length before they are located in hollow needles. U.S. Pat. No. 5,938,583 to Grimm discloses a hollow needle that is particularly easy to fill and withdraw. U.S. Pat. No. 6,010,446 discloses a bio-absorbable spacer seed between the seeds that allows a time-related manufacture of seed strands.

A product description for "RADIOACTIVE SEED SHUTTLE" of Messrs MED-TEC (P.O. Box 320, Orange City, Iowa 51041, U.S.A.) discloses a corresponding product whose mode of function, however, is not described. Furthermore, a product description for "EXPRESS SEEDING CARTRIDGE" from the year 1999 of Messrs Indigo Medical Inc. (10123 Alliance Road, Cincinnati, Ohio, 45242) discloses a pre-loaded seed cartridge for the direct filling of a needle.

Referring back to the various methods of inserting seeds, the second conventionally employed method of inserting seeds involves the insertion of hollow needles through which individual seeds (e.g., free seeds) are later discharged at the needle tip. In this case, the individual seeds are discharged individually and manually by way of an apparatus at the needle tip. After this, the needle is withdrawn via a mechanical raster, manually in accordance with the planned seed clearance in the planning raster before the next individual seed is discharged. The individual seeds are re-loaded by way of a spring-based magazine. Such an apparatus is disclosed in U.S. Pat. No. 5,860,909.

In addition, U.S. Pat. No. 6,102,844 discloses a solution whereby the manual discharge of the seeds is fibre-optically monitored. In this case, and contrary to the method disclosed in U.S. Pat. No. 5,860,909, a revolver magazine is used which is very mechanically sophisticated. In addition, WO 00/61229 A1 discloses the taking of different seeds and/or seeds mixtures for the treatment. The position of the needle relative to a position reference block is visually illustrated in this case, as is the detection of an optimal seed deposit position. The selection of a magazine and a seed to be discharged from the revolver magazine is determined from the current position of the needle in the tissue. Furthermore, U.S. Pat. No. 5,906,574 discloses how the establishment of the connection to the treatment plan for an optimal treatment can be derived.

Conventionally, the seeds are supplied punctually at certain days of treatment upon the order of the doctor who is performing the treatment for a respective patient. The order is based on an approximate calculation of the seed requirement for the patient. The calculation is based on the estimation of the prostate volume via medical image data that has been established, typically, weeks before the actual treatment is performed. However, one problem with this estimation of the prostate volume is that the volume of the prostate can change in the time leading up to the date of treatment.

In practice, there is a considerable risk with regard to the fact that, on the day for the treatment, there are not enough similar seeds (e.g., dosage, half-life period, etc.) readily available for the patient. If there is a shortage of seeds, then the treatment has to be aborted. Unfortunately, this may only be discovered when the patient is in the state of narcosis, the prostate having been newly measured with an ultrasonic probe, and the time-related dosage planning having been carried out.

In addition, the seeds are expensive. They simply cannot be returned to a supplier and, at the present time, they cannot be used for other patients for treatment at a later date. If there are not enough seeds available, then all of the seeds are wasted because the operation cannot be performed. If there are too many seeds, then all of the non-placed seeds are wasted because they cannot be used for further treatment purposes. This is particularly disadvantageous because the very expensive palladium seeds have a short half-life period of just under 3 weeks. The inability to use various dosage values is therefore a financial disadvantage for the patient and for the doctor, and is a considerable treatment risk for the patient.

With the use of exclusively similar seeds (e.g., same dosage, same half-life period, etc.), it is not possible to achieve an optimal dosage distribution in the tissue. In particular, the continually improved early recognition diagnosis and the improved imaging process enable a more adapted dosage distribution. This could take tissue properties into consideration in order to reduce, for example, the risk of incontinence or infertility. In addition, with the known devices, a mixing of radiation sources may be possible in principle but with a very high manual effort, and would involve an unacceptably high risk for the patient.

Another disadvantage of the conventional systems is that all of the systems are designed for a purely manual operation. A changeover to an automatic mode of mixing of various seeds would be a highly complex undertaking.

Furthermore, all of the conventional systems support only the exclusive use of either individual seeds or of seed strands, not both. A simultaneous application of both methods for one patient typically requires an unjustifiable expenditure of effort.

A further disadvantage of conventional systems and methods is that the patient-specific manual mixing and filling of magazines and hollow needles involves a high health risk for the medical-technical personnel. In addition, inaccuracies and errors in communication between responsible staff for the dosage planning, the fillers and the implantologists can occur, and there is also the risk of incorrect seed implanting and incorrect treatment involved.

Compared with procedures involving the implantation of individual seeds, the pre-loading of the needles result in the loss of flexibility in the planning phase if the seed are not exactly deposited, or if they cannot be deposited, as planned. If seeds move after being deposited or if faulty handling or servicing occurs, the pre-loaded needles may negatively impact the quality of the treatment.

STATEMENT OF OBJECTIVES AND SUMMARY OF THE INVENTION

The objective of the present invention is to avoid the known disadvantages of the state of the art and to provide an improved method and an apparatus for the implantation of different seeds (e.g., different material, dosage, half-life period, etc.), as well as the implantation of spacer seeds in the tumour tissue, and to provide an improved method and an apparatus for the positioning of seeds, spacer seeds and stoppers in hollow needles or in devices for the seed strand production, in order to obtain an optimal dosage distribution in the tumour tissue after the seed implantation.

The method of the present invention, according to one example embodiment thereof, describes the positioning of radiation source seeds, spacer seeds and stoppers in hollow needles. Various seeds that are separately contained in magazines according to the isotope type (e.g., material, dosage, half-life period), are provided to the hollow needle. The individual magazines may be changed by means of a magazine changer. The magazine changer is located in a changer guide in a position that is perpendicular, e.g., vertical, to the direction of injection of the seeds. The location (e.g., position and orientation) of the needle is measured relative to a location reference block. An optimal seed deposit position is detected acoustically and/or visually and/or in a tactile manner. The selection of a magazine and a seed to be discharged from the magazine is derived from the current position of the needle in the tissue and from a treatment plan for a dosage distribution, which may be established in list form with details on the seed type and the x-y-z-coordinates relative to the location reference block.

The apparatus of the present invention, according to one example embodiment thereof, is configured to position radiation sources (seeds), spacer seeds and stoppers in hollow needles and to discharge the same from the hollow needles. A magazine changer pickup has a guideable magazine changer with magazines arranged in a changer guide in a position that is perpendicular, e.g., vertical, to the injection direction of the seeds. The magazines contain various seeds that are individually separated according to isotope type (e.g., material, dosage, half-life period, etc.). The magazine changer pickup indicates a needle pickup for a hollow needle onto which the magazine changer pickup is flanged by way of a snap closure. The needle can receive seeds from one of the magazines and discharge these seeds by way of a discharge device such as a discharge wire or a discharge stiletto. The magazine changer pickup is connected to a skid with a slide guide for the reproducible and exact positioning of the needle.

The method and the apparatus of the present invention may be advantageously employed for the treatment of prostate cancer with weak radioactive radiation sources (e.g., seeds).

The present invention also enables the mixing of seeds of various types such as iodine or palladium with different half-life periods and dosages. As a result, remaining seeds from previous operative processes can still be used as required. This has a cost-reducing effect. The risk for treatment stoppages before or after the administration of anesthesia resulting from lack of seeds is reduced accordingly.

In addition, the present invention enables the use of radiation sources with different half-life periods and different radiation dosages. With this method, some tissue regions can be radiated for shorter periods of time but at a higher intensity, and others can be radiated for longer periods of time but at a lower intensity, depending on which tissue therapy would appear most beneficial. With the free mixing of seeds, an optimal dosage distribution in the tissue can be planned and achieved. Side effects such as new formation of tumours or incontinence are reduced with the treatment of prostate cancer.

Furthermore, the dosage planning can be immediately corrected and adapted as well as after each seed discharge.

Individual seeds in hollow needles can be used, and hollow needles can be filled time-related with different seeds. An improved treatment result is achieved because the dosage planning is constantly updated. A corresponding planning of the dosage distribution with the new system can be very easily realised.

The seeds can be mixed with stopper seeds and spacer seeds. This has the advantage that, with one needle, even larger interim spaces can be realised than without seeds and spacer seeds. Also, the applicator can be completely automated with a very minimum amount of effort.

The automated discharge of the seeds at pre-planned positions, the co-recording (protocol) and the feedback into the planning reduce the risk of incorrect treatment and increases the quality of the therapy. The error quota is reduced. Verifiable treatment results are obtained and the required concentration threshold is lowered.

Furthermore, the use of seeds with varying dosage and half-life period also simplifies the production of the seeds because, during the production itself, the actual individual seed dosage can be measured and a larger portion of the seeds from the production makes its way to the patient for treatment.

The radiation effects and the health risk for the personnel during manual filling are subsequently reduced.

BRIEF DESCRIPTION OF THE DRAWINGS

The invention is described as follows in greater detail with an example embodiment of an applicator.

DETAILED DESCRIPTION OF THE DRAWINGS

Figure 1:
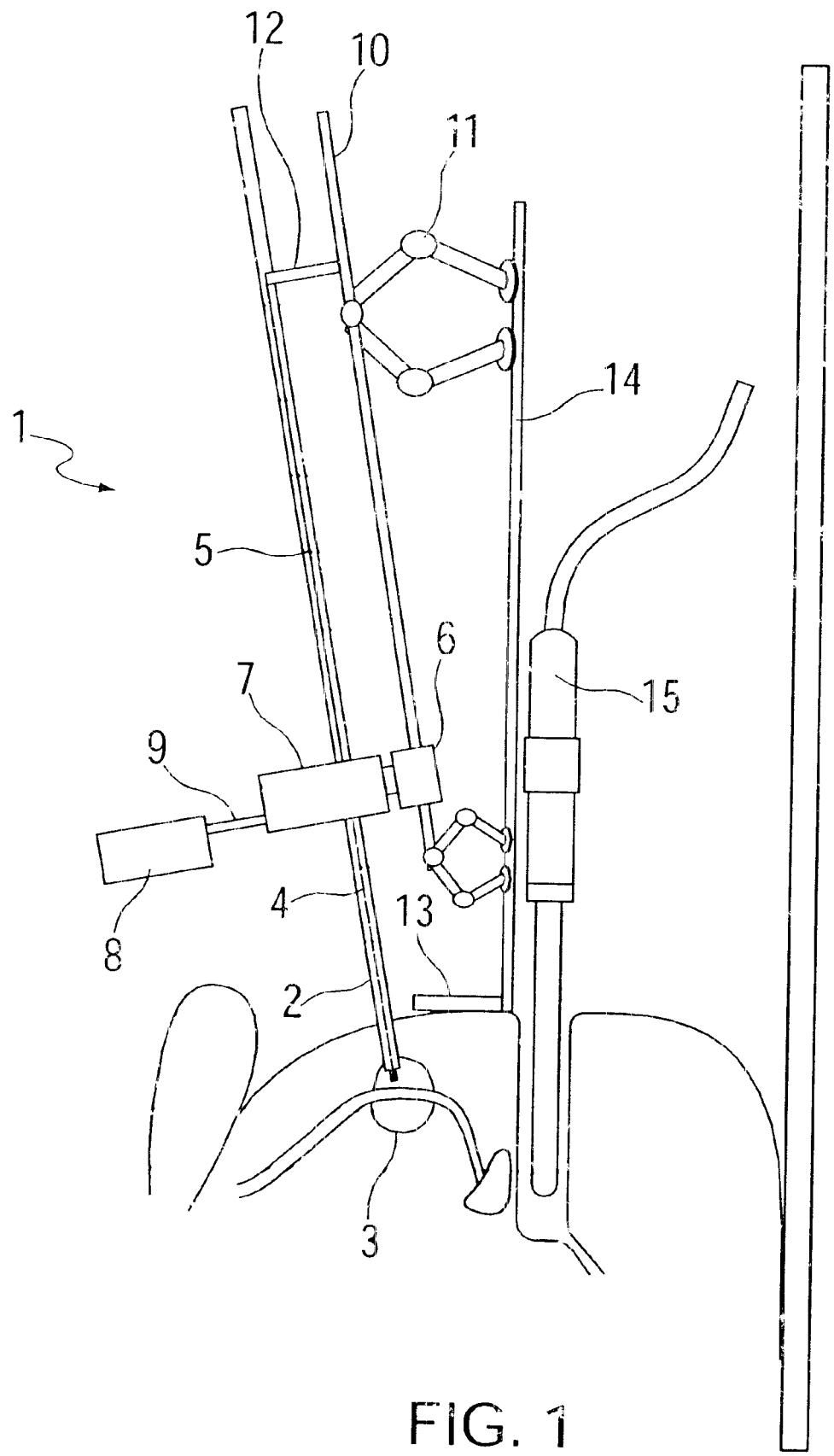
FIG. 1 illustrates a seed applicator with a needle disposed in a tissue, in accordance with one example embodiment of the present invention.

FIG. 1 shows an example embodiment of an applicator 1, according to the present invention. Accordingly, the applicator 1 mainly consists of a magazine changer pickup 7 with a magazine changer 9 with magazines 8, a skid 6 with a linear and a slide guide 10, respectively, with fixation elements 11 on a plate 14, position reference blocks 13, a needle pickup 17 (best shown in FIG. 2) for a hollow needle 2 with discharge device 5 for seeds 4 with a brake 12.

In FIG. 1, the seeds applicator 1 is shown having a flange-type coupling with the hollow needle 2. The hollow needle 2 is shown as being located in the prostate tissue 3. A seed 4 is pressed by way of the discharge device 5 from the magazine 8 and through the needle 2 into the tissue 3.

The entire seed applicator 1 can be drawn out linearly in the direction of the needle from the tissue 3. This is performed via the skid 6 which is attached to the magazine changer pickup 7 of the seed applicator 1.

The skid 6 slides on the linear guide 10 which can be stably secured, by way of the fixation elements 11, in every required position (position and orientation) relative to the position reference block 13. In FIG. 1, this is performed by way of hinged brackets 11 which stabilize, in the front and in the rear, the linear guide 10 on a plate 14 which is fixedly connected with the position reference block 13. By way of the brake 12, the discharge device 5 can be determined relative to the position reference block 13 and/or the linear guide 10.

The position reference block 13 has a known geometry whose relative position to the imaging systems and route measuring systems is known. Instead of the hinged brackets 11, active positioning actuators for the alignment of the linear guide 10 can also be used. The skid 6 can also be driven and braked by way of an actuator.

The discharge device 5 may be a wire-type or stiletto-type instrument, and can be motor-driven and motor-braked. This is advantageous when the needle 2 is pre-loaded in the tissue. The position of the discharge device 5 opposite the position reference block 13 can be determined by reference to the fixation element 11. This is advantageous when the preloaded needle 2 is drawn out of the tissue 3. The position of the needle 2 in the tissue 3 can be detected via a rectal probe 15. The position of the applicator 1 can also be calculated by way of geometric considerations from the ultrasonic image and derived from the movement path of the needle 2. The movement of the applicator 1 can be measured via route measuring systems on the linear guide 10.

Figure 2:
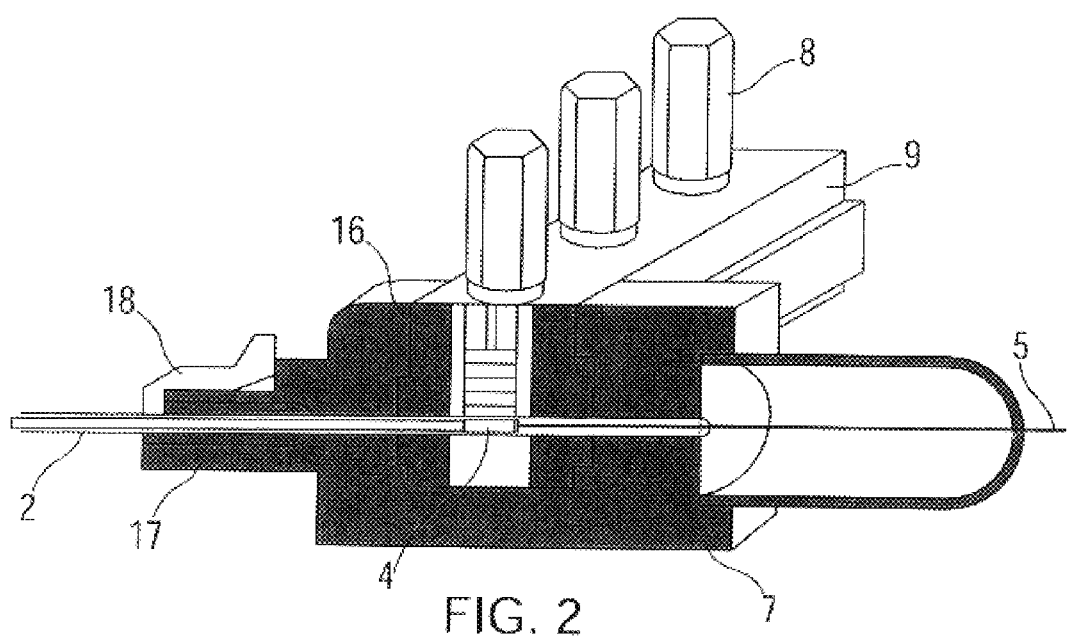
FIG. 2 illustrates a magazine changer pickup of the seed applicator illustrated in FIG. 1.

FIG. 2 shows the magazine changer pickup 7 of the seed applicator 1 and a magazine changer 9 with seed magazines 8 in the cross-sectional view. The seed magazines 8 are fitted in the magazine changer 9. The magazine changer 9 slides in a changer guide 16. The operable positions of the magazine changer 9 in the changer guide 16 are obtained by way of a servo- and raster mechanism. In the operable positions, a single seed 4 can be pressed by way of the discharge device 5 into the needle 2.

The needle 2 is fixedly positioned in the needle pickup 17 by way of a snap closure 18. The magazine changer 9 slides in the linear guide 10 in the magazine changer pickup 7 and brings, in each case, a magazine 8 into position in front of the discharge device 5. A ball notch secures the exact position of the individual magazine 8 in front of the discharge device 5. The discharge device 5 pushes the seed 4 out of the magazine 8 and brings it into the required position in the needle 2 and/or discharges it at the needle tip. The position of the discharge device 5 relative to the needle reference point is detected by way of a scale. The needle 2, in its position to the needle reference point, is secured by way of the snap closure 18 in its position.

Figure 3:
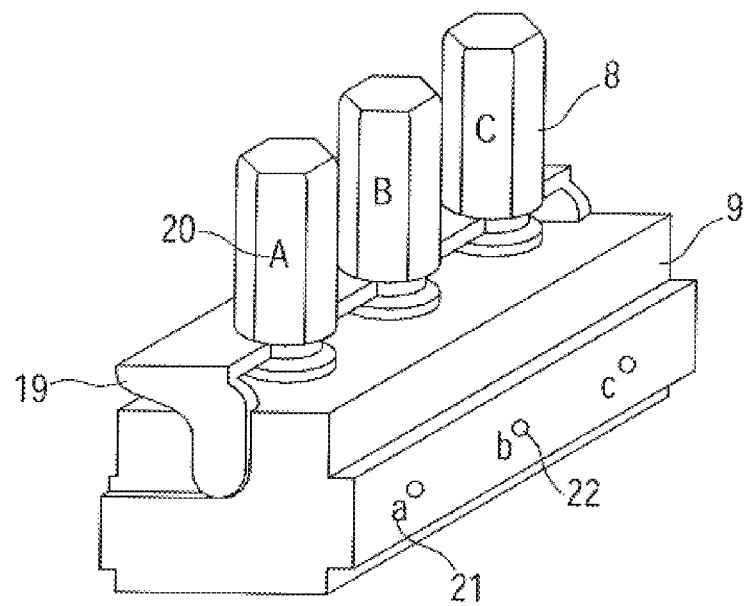
FIG. 3 illustrates a linear execution of the magazine changer illustrated in FIG. 1 and FIG. 2.

FIG. 3 shows a magazine changer 9 with a linear arrangement of the magazines 8. A notch-type locking bracket 19 secures the position 22 of the magazines 8 in the magazine changer 9. A sensor detects whether the locking bracket 19 is open or closed. Preferably, the magazine changer 9 can only be moved when the locking bracket 19 is closed. An attached position code 21 on the changer 9 and/or on the linear guide 10 and a sensor allow the recognition of the magazine position in front of the discharge device 5. An attached magazine code 20 and a sensor allow the recognition of the magazine 8 in the magazine position in front of the discharge device 5. Preferably, the discharge device 5 can only be moved forward when the locking bracket 19 is closed, and when the magazine position and the magazine type are known.

Instead of the insertable magazines 8, hoses or other feed mechanisms can also be used, with which the seeds 4 are transported into the magazine changer 9. For instance, in a further embodiment of the magazine changer 9, not shown here, the magazines 8 are not located on a linear axis but on an orbital path instead (e.g., a revolver changer).

Figure 4:
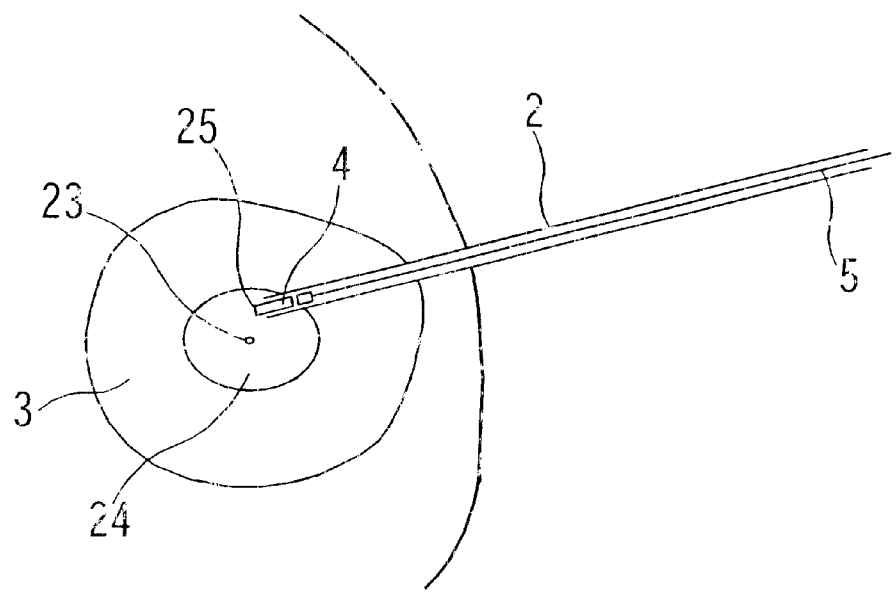
FIG. 4 illustrates a position-controlled discharge of seeds in the tissue, in accordance with one example embodiment of the present invention.

FIG. 4 shows the discharge of single seeds 4 in the tissue 3. The needle 2 is located in the tumour tissue and is drawn back until the seed position 25 for a seed 4 to be discharged has, in front of the needle tip, a minimum clearance to a pre-planned Cartesian position 23 relative to a position reference block 13 (as shown in FIG. 1), such that an allowed tolerance interval 24 is not exceeded.

The position of the needle 2 relative to the position reference block 13 is continually detected by way of an internal measuring system (e.g., an encoder), an external measuring system (e.g., an optical navigation system) or a relative measuring system (e.g., an ultrasonic position of the needle tip in the tumour tissue).

The position of the discharge device 5 in the needle 2 may be continually detected by way of an internal measuring system (e.g., an encoder, notch scale, etc.).

Figure 5:
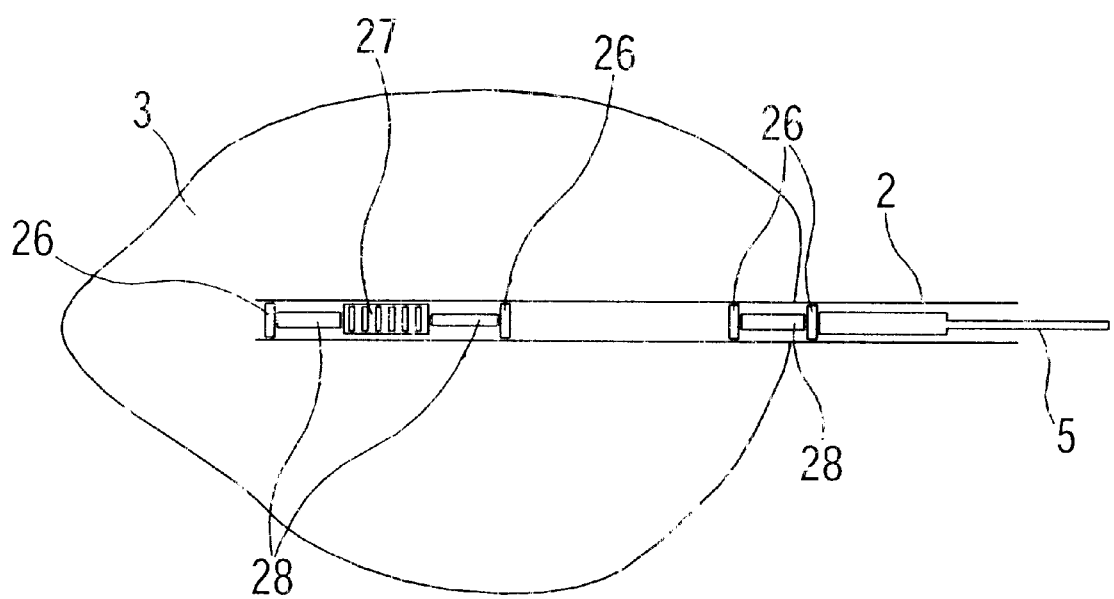
FIG. 5 illustrates the filling of needles for several tumour areas and tissue, in accordance with one example embodiment of the present invention.

FIG. 5 shows the filling of a needle 2 with stoppers 26, active seeds 4 and spacer seeds 27 for two tissue areas. Both tissue areas can be filled with a single needle 2. For discharging purposes, the discharge device 5 is mechanically fixedly positioned relative to the position reference block 13. Following this, the needle guide with the needle 2 is withdrawn.

For the application of single seeds 4, the applicator 1 may be used as described below. From the dosage planning stage, it is known which seed magazine 8 (e.g., which seed type, dosage, half-life period and quantity) are currently available for treatment purposes. By way of the dosage planning, this data is employed in order to establish the current treatment plan.

The hollow needle 2 is inserted up to its maximum pre-planned penetration depth into the tissue 3. The position and orientation of the needle tip relative to the position reference block 13 is known. The position and orientation of the tumour tissue relative to the position reference block 13 is also known.

The current treatment plan is typically pre-determined. The current treatment plan may comprise a list of all seeds 4 to be placed, with details of the seed type (e.g.: iodine, palladium, spacer, stopper) as well as the x, y, and z-coordinates (depth) of the position of the seeds 4 relative to the position reference block 13. A spatial tolerance interval for each seed position may also be pre-determined, outside of which a seed 4 shall not be deposited.

The applicator 1 may be flangedly coupled onto the needle 2 by way of a snap closure 18. The needle 2 is drawn back until the needle tip is positioned in such a way that a seed 4 to be discharged at the needle tip is as close as possible, e.g., is within a minimal clearance interval, to a seed position 23 as planned in the treatment plan. The magazine 8 of the relevant seed type is then brought into position in front of the discharge device 5 by the magazine changer 9. With the discharge device 5, the seed 4 is pressed out of the magazine 8 and put through the hollow needle 2 at the needle tip into the tissue 3.

The position 25 (as shown in FIG. 4), at which the seed 4 was actually positioned, is signalled back to the dosage planning system. Optionally, at least the position of the needle tip in the tissue is known by way of an imaging system, in order to detect positional changes of the tissue compared with the position reference block and to give full consideration here for the planning and seed placing.

The dosage planning system can then generate a new updated treatment plan. This is done with due consideration of all seeds 4 already placed and those which are yet to be placed. It is also done on the basis of seeds 4 existing locally and still in the magazine 8.

If all seeds 4 of a magazine 8 are used up, the user is then called on to insert a new seed magazine 8 into the magazine changer 9.

The withdrawal of the needle 2, the displacement of the magazine changer 9 and the discharge of the seeds 4 by way of the discharge device 5 can be performed by motor if required in order to support partial processes or the entire process.

For pre-loading the hollow needles 2, the apparatus may be used as described below. The hollow needle 2 is inserted up to its maximum pre-planned penetration depth into the tissue 3. The position and orientation of the needle tip relative to the position reference block 13 is known. The position and orientation of the tumour tissue relative to the position reference block 13 is also known.

The current treatment plan is known in advance. The current treatment plan is a list of all seeds to be placed, with details of the seed type (e.g., iodine, palladium, spacer, stopper) as well as the x, y, and z-coordinates (e.g., depth) of the position of the seeds 4 relative to the position reference block 13. A spatial tolerance interval for each seed position has been pre-determined, outside of which a seed 4 shall not be deposited.

The applicator 1 may be flangedly connected onto the needle 2 by way of a snap closure 18. The hollow needle 2 is then filled with seeds 4 as well as spacers 27 in such a way that the seeds 4 in the needle 2 have a minimal clearance to a seed position 23 as planned in the treatment plan. The magazine 8 of the relevant seed type (stopper 26, isotope 28 or spacer 27) with the magazine changer 9 is then brought into position in front of the discharge device 5. It is then calculated in which position in the needle 2 a seed 4 has to be positioned. With the discharge device 5, the seed 4 is pushed out of the magazine 8 to the location in the hollow needle 2 which is planned for the seed 4 or the spacer 27. If the needle 2 is adequately filled, the discharge device 5 remains stationary in the needle 2 in order to support the seeds 4 in their position in the needle 2. Now, the hollow needle 2 is drawn back slowly from the tissue 3. However, the discharge device 5 maintains its position relative to the position reference block 13. Here, the seeds 4 are deposited in the tissue 3.

The position 25, at which the seed 4 was actually positioned, is signalled back to the dosage planning system. Optionally, at least the position of the needle tip in the tissue is known by way of an imaging system, in order to detect positional changes of the tissue compared with the position reference block and to give full consideration here for the planning and seed placing.

The dosage planning system can then generate a new updated treatment plan. This is performed with due consideration of all seeds already placed and those which are yet to be placed. It is also performed on the basis of seeds existing locally and still in magazines.

If all seeds of a magazine are used up, the user is then called on to insert a new seed magazine into the magazine changer.

The withdrawal of the needle, the displacement of the magazine changer and the discharge of the seeds by way of the discharge device 5 can be performed by a motor if required in order to support partial processes or the entire process.

Compared with the individual seeds, the pre-loading of the needles may result in the loss of flexibility in the planning phase if the seeds, as planned, are not exactly deposited or if they cannot be deposited. If seeds move after being deposited or if faulty handling or servicing occurs, the pre-loaded needles may be a disadvantage for the treatment quality.

The applicator can also be used, according to one example embodiment of the present invention, for the production of seed strands and the extra-corporal pre-loading of hollow needles.

The method according to the invention can also be used, according to one example embodiment, for the extra-corporal filling of needles if the filled needles are later navigated and inserted at pre-planned positions and conventionally unloaded.

The method according to the invention can also be used, according to one example embodiment, for depositing seeds in bio-absorbable materials, from which seed strands with bio-absorbable spacer and connecting elements can be produced.

What is claimed is:

1. A method for positioning in a tissue a radiation seed via a hollow needle in accordance with an established treatment plan, wherein the established treatment plan is a plan of the types and coordinate positions of the seeds to be used to treat the tissue, said method comprising the steps of:

separately disposing different types of seeds in magazines depending on at least one of the isotope type, material, dosage, and half-life period of the seeds;

determining the current position of the needle in a tissue relative to a position reference block;

determining, from the current position of the needle in the tissue relative to the position reference block and from the established treatment plan, a type and a position of a seed to be deposited;

selecting the magazine corresponding to the determined seed; and providing the determined seed to the hollow needle from the selected magazine.

2. The method according to claim 1, wherein the method also positions spacer seeds in the tissue.

3. The method according to claim 1, wherein the method also positions stoppers in the tissue.

4. The method according to claim 1, wherein the needle includes a discharge device which moves linearly independently from the linear movement of the needle, the method further comprising the step of discharging the seed in the tissue via the discharge device.

5. The method according to claim 4, further comprising the step of determining the location of the discharge device via its position relative to a slide guide.

6. The method according to claim 4, further comprising the step of determining the location of the discharge device via its position relative to a position reference block.

7. The method according to claim 4, further comprising the steps of:

signalling back to a dosage planning software the position of the discharged seeds; and updating the treatment plan.

8. The method according to claim 1, wherein the orientation of the magazine changer is fixedly positioned relative to a position reference block, said method further comprising the step of moving the magazine changer linearly backwards.

9. The method according to claim 1, further comprising the step of determining the location of the magazine changer via its position relative to a position reference block.

10. The method according to claim 1, further comprising the steps of:

measuring the position of the magazine changer; and detecting the magazine type.

11. The method according to claim 1, further comprising the step of applying spacer seeds and stoppers made of bio-absorbable materials.

12. The method according to claim 1, further comprising the step of transporting the seeds into the magazine chamber via a feed mechanism.

13. The method according to claim 12, wherein the feed mechanism is a hose.

14. The method according to claim 1, wherein the step of providing the seeds to the hollow needle is performed on a non-linear axis.

15. The method according to claim 14, wherein the non-linear axis is an orbital axis.

16. An apparatus for positioning radiation source seeds, spacer seeds and stoppers in a hollow needle and for discharging the same from the hollow needle, comprising:

a plurality of magazines containing various seeds individually separated according to at least one of isotope type, material, dosage, and half-life period;

a magazine changer pickup with a guideable magazine changer having the magazines arranged in a changer guide in a position which is vertical relative to the injection direction of the seeds;

a hollow needle;

a needle pickup for coupling the hollow needle to the magazine changer pickup;

a discharge device coupled to the needle;

wherein the apparatus is configured such that the needle receives seeds from one of the magazines and discharges the seeds via the discharge device through the needle; and a skid coupled to the magazine changer pickup and to a slide guide for determining the position of the needle.

17. The apparatus according to claim 16, wherein the magazine changer is configured to be operable by one of manually and by motor, and wherein the magazine changer is adjustable.

18. The apparatus according to claim 16, wherein the discharge device is configured to be operable by one of manually or by motor, and wherein the discharge device is one of adjustable and fixedly positionable.

19. The apparatus according to claim 16, wherein the position of the magazine changer pickup on the slide guide is configured to be operable by one of manually or by motor, and wherein the magazine changer pickup is one of adjustable and fixedly positionable.

20. The apparatus according to claim 16, wherein the position of the apparatus is configured to be operable by one of manually or by motor, and wherein the apparatus is one of adjustable and fixedly positionable.

* * * * *